United States Patent [19]

Muenster

[11] 4,061,849
[45] Dec. 6, 1977

[54] PROCESS FOR THE RECOVERY OF GASEOUS OR VAPOROUS MONOMERS FROM REACTION OFF-GASES

[75] Inventor: Alfred Muenster, Ludwigshafen, Germany

[73] Assignee: BASF Aktiengesellschaft, Ludwigshafen (Rhine), Germany

[21] Appl. No.: 670,249

[22] Filed: Mar. 25, 1976

[30] Foreign Application Priority Data

Mar. 29, 1975 Germany ............................. 2514126

[51] Int. Cl.² ............................. C08F 2/18; C08F 6/00
[52] U.S. Cl. ......................................... 526/68; 203/42; 526/77; 526/328; 526/330; 526/340
[58] Field of Search ....................... 526/68, 77; 203/42

[56] References Cited

U.S. PATENT DOCUMENTS

| 3,109,837 | 11/1963 | Lockheed et al. | 526/77 |
| 3,255,171 | 6/1966 | Eilbracht et al. | 526/68 |
| 3,642,736 | 2/1972 | Downs | 526/68 |

Primary Examiner—Alan Holler
Attorney, Agent, or Firm—Keil, Thompson & Shurtleff

[57] ABSTRACT

Gaseous and/or vaporous monomers are recovered from reaction off-gases by treating the latter with compounds which are liquid at 50° C and atmospheric pressure and with which, and/or in which, the said monomers are subsequently reacted.

10 Claims, 1 Drawing Figure

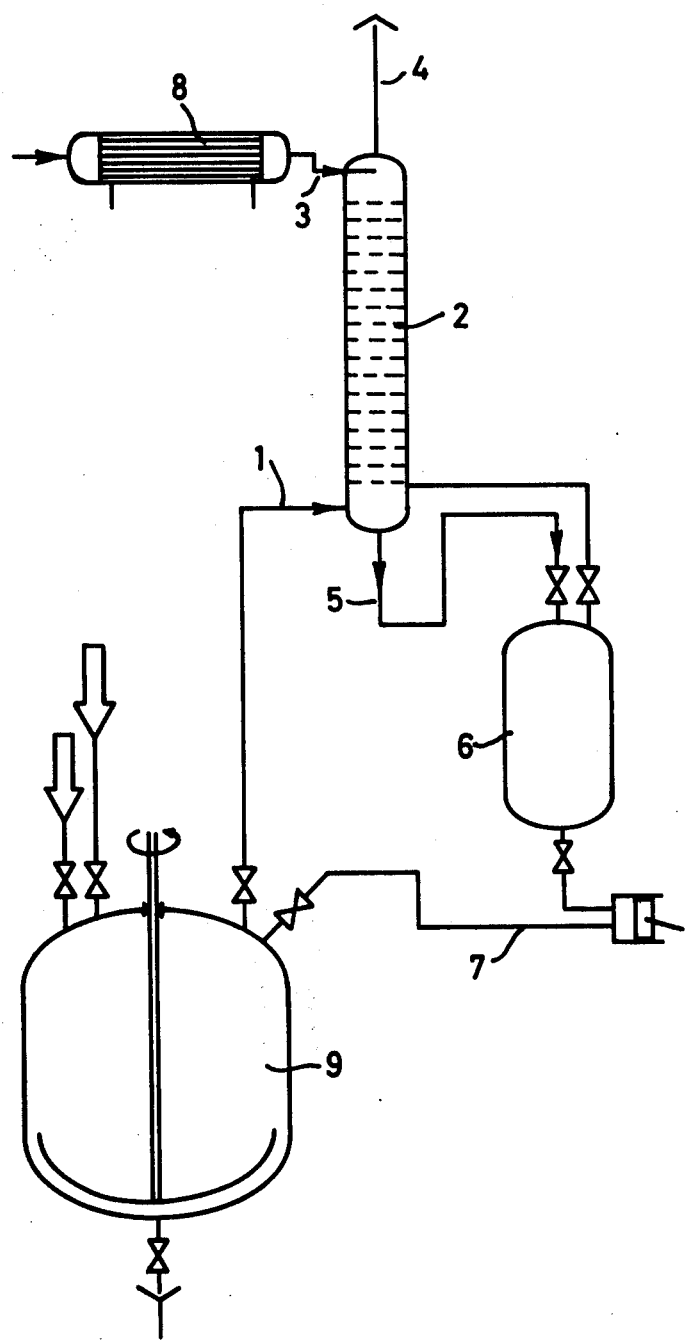

PROCESS FOR THE RECOVERY OF GASEOUS OR VAPOROUS MONOMERS FROM REACTION OFF-GASES

Homopolymers and copolymers of monomers which are gaseous at 25° C and atmospheric pressure are manufactured on a large scale, especially by emulsion, solution or suspension polymerization processes. These are generally carried out under pressure and the monomers and comonomers are, in most cases, emulsified in water or — in the case of suspension polymerization — suspended in the form of larger droplets. Where solutions of such gaseous or very volatile monomers are produced, the process is again generally carried out under pressure, and suitable inert organic solvents, which are liquid at 25° C and atmospheric pressure, are used, examples being acetone, ethyl acetate, n-butyl acetate and liquid hydrocarbons, e.g. hexane. Monomers which are gaseous or very volatile under normal conditions are, above all, vinyl chloride, isobutylene, butadiene, vinylidene chloride, ethylene, propylene, isoprene and vinyl methyl ether. Suitable comonomers for these are, above all, vinyl-aromatic compounds, especially styrene and α-methylstryrene, acrylic and methacrylic compounds, e.g. acrylic acid and methacrylic acid and their water-soluble salts, amides, N-alkylolamides, nitriles, alkyl esters and hydroxyalkyl esters, e.g. sodium acrylate, methyl acrylate, ethyl acrylate, n-butyl acrylate, 2-ethylhexyl acrylate, dodecyl acrylate, methyl methacrylate, n-butyl methacrylate, 2-ethylhexyl methacrylate, β-hydroxyethyl acrylate, β-hydroxypropyl acrylate, β-hydropropyl methacrylate, acrylamide, methacrylamide, acrylonitrile, methacrylonitrile, N-methylolacrylamide, N-n-butoxymethylacrylamide, N-methoxymethyl-methacrylamide and vinyl esters, e.g. vinyl acetate, vinyl propionate, vinyl n-butyrate and vinyl laurate, and also vinyl ethers, such as vinyl ethyl ether.

In the manufacture of copolymers from monomers of the stated type, the monomer or monomer mixture which is liquid under normal conditions is dispersed in water, in the presence of emulsifiers and/or protective colloids, or dissolved in water or organic solvents, in a stirred vessel. The gaseous monomer is then forced in, as is also, in most cases, an inert gas, in general nitrogen. The mixture is then, in industrial practice, transferred to a polymerization vessel, the pressure in the vessel where the monomer solution or emulsion is first prepared being kept constant by introducing an inert gas. When manufacturing copolymers of vinyl chloride or butadiene, the pressure is from 8 to 10 atmospheres gauge, whilst for the manufacture of vinylidene chloride polymers it is from 0.5 to 2 atmospheres gauge. After completion of the polymerization reaction, during which the monomer mixture is forced into the polymerization vessel from the feed vessel, the latter contains a gas mixture which, depending on the monomers and temperatures used, contains from 10 to 50 percent by volume of the gaseous monomer. Before refilling the feed vessel the internal pressure must be reduced to normal pressure, and in doing so, in an amount of gaseous monomer which, depending on the size of the feed vessel and on the pressure, is up to 100 kg per batch, or more, generally escapes into the atmosphere. If, e.g., the feed vessel has a capacity of 10 m³ and, after discharging therefrom an aqueous vinyl chloride emulsion, is still at a pressure of 10 atmospheres gauge and a temperature of 20° C, the off-gas which escapes on letting down to atmospheric pressure contains 97.48 kg of vinyl chloride if the gas space of the vessel is saturated with vinyl chloride. In practice, the gas mixture is in most cases about 50% saturated with gaseous monomer. In industrial installations, this procedure results in many tons of monomers per annum being released into the atmosphere with the off-gas. This is true, above all, in the case of large scale products based on vinyl chloride, butadiene or vinylidene chloride.

Processes which reduce the amounts of these gaseous or vaporous monomers in the reaction off-gases have therefore already been proposed. For example, it has been proposed to pass the off-gases to a combustion unit and burn them therein, if necessary after admixture of air. However, in the case of chlorohydrocarbons, such as vinyl chloride and vinylidene chloride, this measure is practically inapplicable because of the combustion gases containing hydrogen chloride and therefore requiring a water wash. It has also been proposed to absorb the reaction off-gases on materials having an active surface, and to desorb them periodically by means of steam, in which case the desorbate must subsequently be cooled and compressed to liquefy it. It is also possible to wash the monomers out of the off-gas by means of inert solvents, e.g. water or wash oils, but this must be followed by expensive working up of the solutions. Finally, the off-gases can also be cooled to low temperatures in order to condense the gaseous and/or vaporous monomers contained therein. However, all these processes are very expensive because of the apparatus required, the space required and the operating costs, and their utility is poor in relation to cost.

It is an object of the present invention to recover gaseous and/or vaporous monomers contained in reaction off-gases, e.g. in feed vessels of the above type, at little cost.

We have found that this object is achieved and that gaseous and/or vaporous monomers can be recovered from reaction off-gases in an advantageous manner by treating, e.g. extracting, the reaction off-gases with organic materials which are liquid at 50° C and atmospheric pressure and with which, and/or in which, the said monomers are subsequently reacted. The new process is of particular importance for the recovery of vinyl chloride (bp −13.9° C), butadiene (bp −3° C) and vinylidene chloride (bp 31.5° C), and also of vinyl methyl ether (bp 6° C), isobutylene (bp −6°) and isoprene (bp 34° C). The process can also be applied to ethylene and propylene, but the efficiency is less good because of the extremely low boiling points of these monomers. Therefore the new process is especially useful for the recovery of polymerizable olefinically unsaturated monomers having boiling points at atmospheric pressure between −20° C and +40° C, especially between −15° C and +35° C. Organic materials which can be used for the treatment of the reaction off-gases, e.g. organic compounds which are liquid at 50° C under atmospheric pressure, are, advantageously, olefinically unsaturated comonomers as specified above. Comonomers of particular interest for this purpose are those from the group of styrene and monoolefinically unsaturated monocarboxylic acid esters of 4 to 8 carbon atoms, e.g. vinyl acetate, vinyl propionate, ethyl acrylate, methyl methacrylate, isopropyl acrylate, n-butyl acrylate, iso-butyl acrylate and n-butyl methacrylate. The comonomers may be employed as such or as solutions in organic inert solvents which are suitable media for a solution polymerization, and also as emulsions in aqueous media or in suitable inert organic liquids, and as suspensions in water or suitable inert organic liquids, in which case the conventional emulsifying assistants and/or dispersing assistants, e.g. emulsifiers and/or protective colloids, may be present. Organic inert solvents which are liquid under atmospheric pressure at 50° C and are suitable media, i.e. diluents, for a solution polymerization can also be used for the treatment of the reaction off-gases. Examples of these are benzene, hexane cyclohexane, cyclohexanone, acetone, ethyl acetate, n-butyl acetate, dioxane, methyl ethyl ketone and mixtures of such compounds. These solvents may also be used as mixtures with olefinically unsaturated comonomers.

The treatment of the reaction off-gases with the liquid organic material, i.e. the comonomers and/or the solvents or the aqueous emulsions or suspensions of the comonomers, may be carried out, e.g., in the feed vessels or in separate stirred vessels, and it is of advantage to cool the mixtures to from −20° C to +5° C, especially to about 0° C, and stir them for some time, e.g. from 10 to 30 minutes. The liquid phase then becomes saturated with the monomer present as gas or vapor, and as a result the residual gas in the feed vessel or stirred vessel becomes depleted in the gaseous or very volatile monomer. The residual gas can then be released into the atmosphere or can, if necessary, be purified further; e.g., in the case of butadiene a subsequent wash with water in a scrubber removes the butadiene practically completely from the off-gas. It is also possible to wash the reaction off-gas, e.g. from the feed vessel, in countercurrent with the monomers and/or solvents in a column provided with packings or bubble-cap trays, in which case the gas issuing from the top of the column is substantially free from the gaseous or vaporous monomers, especially if the column is charged with cooled comonomers and/or cooled solvents. In a similar manner, reaction off-gas resulting from, e.g., the deodorizing of dispersions of copolymers of vinyl chloride, vinylidene chloride or butadiene, can be substantiallly freed from residues of these monomers.

Using the new process it is possible very substantailly to recover gaseous and/or vaporous monomers from reaction off-gases, with particularly low cost of apparatus, especially if the recovery is carried out in vessels which are present in any case, e.g. in feed vessels. The gaseous and/or vaporous monomers are obtained as a mixture with monomers or solvents with which, and/or in which, they are subsequently reacted. Further expensive working-up is therefore not necessary in the new recovery process. In addition to the recovery of the monomers, a particularly important aspect is that the off-gas is substantially purified.

The process according to the invention is illustrated in the Examples which follow:

EXAMPLE 1

4,200 liters of a 40% strength aqueous styrene emulsion, using a conventional emulsifier and further conventional additives, are prepared in a stirred vessel (feed vessel) of 10 m³ capacity, at 25° C, and 2,000 kg of butadiene are added. The pressure in the stirred vessel is then raised to 10 atmospheres gauge with nitrogen. In the course of 8 hours the emulsion is fed, simultaneously with a conventional aqueous initiator solution, into a polymerization vessel, where a dispersion, of about 50% strength, of a copolymer of styrene and butadiene is obtained. During the entire feed time, the pressure in the feed vessel is kept at 10 atmospheres gauge by further introduction of nitrogen.

When all the material has been run into the reactor, a mixture of nitrogen and butadiene which contains small amounts of styrene is left in the feed vessel. Theoretically, the partial pressure of the butadiene is 2.98 atmospheres; actually, however, the gas is not saturated with butadiene. The measured values were about 1.64 atmospheres absolute for a molar ratio of styrene to butadiene of 1:2.

10 m³ at 10 atmospheres gauge correspond to 100 m³ (S.T.P.) and contain 16.4 m³ (S.T.P.), equivalent to 38.07 kg, of butadiene.

1,000 liters (907 kg) of styrene — about half of the amount required for one polymerization batch — are now introduced into the feed vessel after cooling to −10° C and are stirred for 15 minutes, the temperature in the vessel assuming a value of +8° C. The stirrer is now stopped and the gas mixture above the liquid, the pressure of which mixture initially rose to 11 atmospheres gauge due to the introduction of 1,000 liters of styrene, but then fell again to 9.1 atmospheres gauge due to the cooling which took place and due to the absorption of the butadiene by the styrebe, is let down through a discharge valve. The off-gas still contains 4.9 kg of butadiene, whilst 33.17 kg of the butadiene are dissolved in the styrene. The latter solution is employed directly for the next polymerization batch.

EXAMPLE 2

The same polymerization reaction as that described in Example 1 for the manufacture of an aqueous styrene-butadiene copolymer dispersion is carried out.

However, in this case the off-gas from the feed vessel is purified in a bubble-cap tray column in accordance with the accompanying drawing.

The feed vessel (9) is vented in the course of 30 minutes, through the line (1), into the lower part of a bubble-cap tray column (2), in which the gas mixture is washed in countercurrent with styrene at 20° C, which is fed to the top of the column through line (3). The gas issuing at the top of the column through line (4) only retains traces of butadiene together with a small amount of styrene (corresponding to a partial pressure of 5.5 mm Hg at 20° C) and can be discharged into the atmosphere without further purification. The styrene laden with butadiene runs from the bottom of the column through line (5) into an intermediate vessel (6), from which it is drawn off again for a subsequent polymerization batch. (If two polymerization lines are available, the styrene can be transferred directly into a second feed vessel, which is not shown). The column is 8 m high, has a diameter of 400 mm and is fitted with 13 bubble-cap trays.

The following quantitative table shows the effect of the process:

Volume of vessel = 10 m³
Pressure = 9.5 atmospheres gauge, T = 25° C

| Total amount of off-gas m³ (S.T.P.) | Butadiene Total kg | Butadiene in off-gas kg | Styrene kg | Off-gas m³ (S.T.P.) | Styrene in off-gas kg |
|---|---|---|---|---|---|
| 95 | (6.71 m³ (S.T.P.)) 15.58 | 0.76 | 1,000 | 88.3 | 2.98 |
| 14.82 | kg of butadiene are dissolved in the styrene. | | | | |

EXAMPLE 3

The procedure followed is as described in Example 2, except that before entering the wash column (2) the stryrene is cooled to 0° C by means of brine in the cooler (8).

The amount of butadiene released in the off-gas consequently drops to 0.23 kg and the amount of styrene, corresponding to a vapor pressure of 1.5 mm Hg, drops to 0.174 m$^3$ (S.T.P.), corresponding to 0.81 kg.

The styrene is in any case present in the off-gas from the feed vessel (9), since the batch in any case contains styrene.

EXAMPLE 4

A 50% strength polymer solution is prepared from a mixture consisting essentially of 60 parts of vinyl chloride and 40 parts of vinyl acetate, using n-butyl acetate as the solvent.

A solution of vinyl acetate in n-butyl acetate is prepared in a feed vessel of 6 m$^3$ capacity; the oxygen is removed by blowing in nitrogen, and the requisite 3mount of liquid vinyl chloride is then added. n-Butyl acetate is first introduced into the polymerization vessel and the monomer mix is added uniformly in the course of 6 hours at 75° C, together with a solution of a conventional organic peroxide in n-butyl acetate. At the same time the pressure in the feed vessel is kept constant at 10 atmospheres gauge. When all the material has been run in, the feed vessel contains 60 m$^3$ (S.T.P.) of a gas mixture consisting essentially of nitrogen and vinyl chloride, in which the vinyl chloride content at 20° C, corresponding to its vapor pressure, is theoretically 19.03 m$^3$ (S.T.P.), corresponding to 53.11 kg of vinyl chloride.

In practise, the equilibrium which is set up is such that the vinyl chloride content is just under 50% of the theoretical amount, manely 9.13 m$^3$ (S.T.P.), corresponding to 25.5 kg.

750 liters of n-butyl acetate at 20° C are now run into the feed vessel. After 15 minutes, the stirrer is stopped and the vessel is vented. The gas mixture leaving the vessel still contains 1.12 m$^3$ (S.T.P.) of vinyl chloride, corresponding to 3.12 kg, in addition to a small amount of n-butyl acetate.

If the extraction is carried out in the feed vessel with n-butyl acetate cooled to −10° C, in which case the internal temperature assemes a value of +6.5° C, the vinyl chloride content in the off-gas drops to 0.47 m$^3$ (S.T.P.), corresponding to 1.33 kg of vinyl chloride (= 5.2% of the initial amount).

The resulting solution of vinyl chloride in n-butyl acetate is used for the next polymerization batch.

Here again, this proportion can be reduced further by the process described in Example 2.

EXAMPLE 5

A 50% strength aqueous dispersion based on a copolymer of 65 parts of vinyl chloride and 35 parts of vinyl propionate is prepared by the method described in Example 1.

An emulsion of vinyl propionate in water is prepared in the feed vessel, vinyl chloride and nitrogen are added and this emulsion is reacted in the conventional manner in a polymerization vessel.

The pressure in the feed vessel, which has a capacity of 8 m$^3$, is 10 atmospheres gauge, and the temperature is 15° C.

When all the material has been run into the reaction vessel, the gas mixture in the feed vessel is 9.6 m$^3$ (S.T.P.), corresponding to 26.8 kg of vinyl chloride. 800 liters of vinyl propionate at +10° C are now introduced into the feed vessel and stirred for 20 minutes, and after stopping the stirrer the gas mixture is let down.

The gas discharged still contains 0.92 m$^3$ (S.T.P.) of vinyl chloride, corresponding to 2.68 kg.

The vinyl propionate used is employed for the next polymerization batch.

EXAMPLE 6

A 50% strength aqueous dispersion of a vinylidene chloride/methyl acrylate copolymer is prepared in the conventional manner using emulsifiers and other conventional additives. The monomer emulsion is prepared in a 10 m$^3$ feed vessel at 20° C and 1 atmosphere gauge, and is fed to the polymerization vessel.

When all the monomer has been run in, the feed vessel contains 20 m$^3$ (S.T.P.) of a gas mixture of nitrogen, methyl acrylate and vinylidene chloride, wherein the vinylidene chloride content (theoretically 30% of the volume at a vapor pressure of 0.65 atmosphere absolute and at 20° C is actually 17.2% by volume, corresponding to 3.44 m$^3$ (S.T.P.) or 14.74 kg.

600 liters of methyl acrylate at +10° C are introduced into the feed vessel, whilst stirring. After 15 minutes, the vinylidene chloride content in the gas mixture is still 1.9% by volume, equal to 0.38 m$^3$ (S.T.P.) or 1.63 kg.

The methyl acrylate, containing vinylidene chloride, is used for the next polymerization batch.

In all the Examples, it is also possible to take the complete mix of liquid monomers and water (emulsion) or solvent and carry out the absorption of the gaseous monomer therein.

I claim:

1. A polymerization process in which a low-boiling olefinically unsaturated monomer having a boiling point at atmospheric pressure between −20° and 40° C is homopolymerized in a liquid material having a boiling point above 50° C at atmospheric pressure, and in which a reaction off-gas is generated containing from 10 to 50 percent by volume of the low-boiling olefinically unsaturated monomer, wherein the reaction off-gas is treated with a liquid material which boils above 50° C at atmospheric pressure and is selected from the group consisting of a solution of the low-boiling monomer in an inert organic solvent, an aqueous emulsion of the low-boiling monomer and an aqueous suspension of the low-boiling monomer, under conditions such that said material does not react with the low-boiling monomer, whereby low-boiling monomer is extracted from the reaction off-gas, and the resulting liquid material containing low-boiling monomer is employed in the polymerization process for manufacture of further amounts of polymer.

2. A process for the recovery of polymerizable olefinically unsaturated monomers having at atmospheric pressure boiling points between −20° C and +40° C from reaction off-gases which contain from 10 to 50% by volume of these monomers, wherein the reaction off-gases are treated with olefinically unsaturated comonomers from the group consisting of styrene and monoolefinically unsaturated monocarboxylic acid esters of 4 to 8 carbon atoms, which comonomers are liquid at 50° C at atmospheric pressure and with which, and/or in which, the olefinically unsaturated low boiling monomers are subsequently reacted.

3. A process as claimed in claim 2 wherein said monomers are low boiling olefinically unsaturated monomers from the group consisting of vinyl chloride, vinylidene chloride, vinyl methyl ether, isobutylene, butadiene and isoprene.

4. A process as claimed in claim 3, in which the liquid, olefinically unsaturated comonomers are employed as a solution in liquid, organic, inert solvents which are suitable media for carrying out a solution polymerization.

5. A process as claimed in claim 3, in which the liquid olefinically unsaturated comonomers are employed as an aqueous emulsion.

6. A process as claimed in claim 3, in which the liquid olefinically unsaturated comonomers are employed as an aqueous suspension.

7. A process for the recovery of polymerizable olefinically unsaturated monomers having at atmospheric pressure boiling points between $-20°$ C and $+40°$ C from reaction off-gases which contain from 10 to 50% by volume of these monomers, wherein the reaction off-gases are treated with inorganic inert solvents which are suitable media for carrying out a solution polymerization and which are liquid at 50° C at atmosheric pressure and in which the olefinically unsaturated low boiling monomers are subsequently reacted.

8. A process as claimed in claim 7 wherein said monomers are low boiling olefinically unsaturated monomers from the group consisting of vinyl chloride, vinylidene chloride, vinyl methyl ether, isobutylene, butadiene and isoprene.

9. A polymerization process in which low-boiling olefinically unsaturated monomer having a boiling point at atmospheric pressure between $-20°$ and $40°$ C is copolymerized with an olefinically unsaturated comonomer in an inert material which is liquid at 50° C, the comonomer and the inert liquid material boiling above 50° C at atmospheric pressure, and in which a reaction off-gas is generated containing from 10 to 50% by volume of the low-boiling olefinically unsaturated monomer, wherein the reaction off-gas is treated with olefinically unsaturated comonomers from the group conisting of styrene and monoolefinically unsaturated monocarboxylic acid esters of 4 to 8 carbon atoms, and which boils above 50° C, under conditions such that said comonomers are liquid and do not react with the low-boiling monomer, whereby low-boiling monomer is extracted from the eaction off-gas, and the reuslting liquid containing low-boiling monomer and comonomers is employed in the polymerization process for manufacture of further amounts of copolymer.

10. A polymerization process in which a low-boiling olefinically unsaturated monomer having a boiling point at atmospheric pressure between $-20°$ and $40°$ C is copolymerized with an olefinically unsaturated comonomer in an inert material which is liquid at 50° C, the comonomer and the inert liquid material boiling above 50° C at atmospheric pressure, and in which a reaction off-gas is generated containing from 10 to 50% by volume of the low-boiling olefinically unsaturated monomer, wherein the reaction off-gas is treated with organic inert solvents which are suitable media for carrying out a solution polymerization and which boils above 50° C, under conditions such that said solvents are liquid and do not react with the low-boiling monomer, whereby low-boiling monomer is extracted from the reaction off-gas, and the resulting liquid containing low-boiling monomer and solvent is employed in the polymerization process for manufacture of further amounts of copolymer.

* * * * *

UNITED STATES PATENT AND TRADEMARK OFFICE
CERTIFICATE OF CORRECTION

PATENT NO. : 4,061,849
DATED : December 6, 1977
INVENTOR(S) : Alfred Muenster

It is certified that error appears in the above-identified patent and that said Letters Patent are hereby corrected as shown below:

Column 8, lines 6-7, "conisting" should read --consisting--
Column 8, line 12, "eaction" should read --reaction--
Column 8, line 12, "reuslting" should read --resulting--

Signed and Sealed this

Twenty-fifth Day of April 1978

[SEAL]

Attest:

RUTH C. MASON
Attesting Officer

LUTRELLE F. PARKER
Acting Commissioner of Patents and Trademarks